United States Patent
Tian et al.

(10) Patent No.: US 10,632,201 B2
(45) Date of Patent: Apr. 28, 2020

(54) IMMEDIATE RELEASE ABUSE DETERRENT FORMULATIONS

(71) Applicant: Capsugel Belgium NV, Bornem (BE)

(72) Inventors: Wei Tian, Lanark (GB); Jenifer Mains, Bathgate (GB); David Robert Sleith, Glasgow (GB)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 16/152,288

(22) Filed: Oct. 4, 2018

(65) Prior Publication Data

US 2019/0117781 A1 Apr. 25, 2019

(30) Foreign Application Priority Data

Oct. 19, 2017 (EP) .................................... 17197292
Oct. 24, 2017 (EP) .................................... 17198033

(51) Int. Cl.
*A61K 47/36* (2006.01)
*A61K 9/48* (2006.01)
*A61K 31/485* (2006.01)

(52) U.S. Cl.
CPC ............ *A61K 47/36* (2013.01); *A61K 9/4825* (2013.01); *A61K 9/4866* (2013.01); *A61K 31/485* (2013.01)

(58) Field of Classification Search
CPC .. A61K 31/485; A61K 9/4825; A61K 9/4866; A61K 47/36
See application file for complete search history.

(56) References Cited

U.S. PATENT DOCUMENTS

| | | |
|---|---|---|
| 6,696,088 B2 | 2/2004 | Oshlack et al. |
| 7,141,250 B2 | 11/2006 | Oshlack et al. |
| 7,144,587 B2 | 12/2006 | Oshlack et al. |
| 7,157,103 B2 | 1/2007 | Sackler |
| 7,332,182 B2 | 2/2008 | Sackler |
| 7,776,314 B2 | 8/2010 | Bartholomäus et al. |
| 7,842,307 B2 | 11/2010 | Oshlack et al. |
| 8,075,872 B2 | 12/2011 | Arkenau-Maric et al. |
| 8,114,383 B2 | 2/2012 | Bartholomäus et al. |
| 8,144,384 B2 | 2/2012 | Arkenau et al. |
| 8,192,722 B2 | 6/2012 | Arkenau-Maric et al. |
| 8,222,292 B2 | 7/2012 | Goskonda et al. |
| 8,329,744 B2 | 12/2012 | Babul |
| 8,420,056 B2 | 4/2013 | Arkenau-Maric et al. |
| 8,475,832 B2 | 7/2013 | Myers et al. |
| 8,529,948 B1 | 9/2013 | Wright et al. |
| 8,563,038 B2 | 10/2013 | Andersen et al. |
| 8,603,526 B2 | 12/2013 | Tygesen et al. |
| 8,895,063 B2 | 11/2014 | Guimberteau et al. |
| 9,044,402 B2 | 6/2015 | Tygesen et al. |
| 9,132,096 B1 | 9/2015 | Rekhi et al. |
| 9,301,918 B2 | 4/2016 | Raman et al. |
| 9,452,135 B2 | 9/2016 | Jacobs et al. |
| 9,511,033 B2 | 12/2016 | Myers et al. |
| 9,573,927 B2 | 2/2017 | Kandula |
| 9,931,303 B1* | 4/2018 | Daniely ............... A61K 9/4866 |
| 2005/0214223 A1 | 9/2005 | Bartholomaeus et al. |
| 2005/0236741 A1 | 10/2005 | Arkenau et al. |
| 2005/0271594 A1* | 12/2005 | Groenewoud ....... A61K 9/4858 424/10.1 |
| 2006/0002860 A1 | 1/2006 | Bartholomaus et al. |
| 2006/0039864 A1 | 2/2006 | Bartholomaus et al. |
| 2006/0051298 A1 | 3/2006 | Groenewoud |
| 2006/0188447 A1 | 8/2006 | Arkenau-Maric et al. |
| 2007/0003616 A1 | 1/2007 | Arkenau-Maric et al. |
| 2007/0065365 A1 | 3/2007 | Kugelmann et al. |
| 2009/0041838 A1 | 2/2009 | Guimberteau et al. |
| 2009/0123386 A1 | 5/2009 | Young |
| 2010/0203129 A1 | 8/2010 | Andersen et al. |
| 2010/0210732 A1 | 8/2010 | Babul |
| 2010/0297232 A1 | 11/2010 | Myers et al. |
| 2011/0033542 A1 | 2/2011 | Myers et al. |
| 2012/0135071 A1 | 5/2012 | Bartholomäus et al. |
| 2012/0308654 A1 | 12/2012 | Bartholomäus et al. |
| 2013/0090349 A1 | 4/2013 | Geißler et al. |
| 2013/0129825 A1 | 5/2013 | Billoet |
| 2013/0129826 A1 | 5/2013 | Geißler et al. |
| 2013/0195935 A1 | 8/2013 | Bartholomäus et al. |
| 2013/0251643 A1 | 9/2013 | Bartholomäus et al. |
| 2013/0280176 A1 | 10/2013 | Diezi et al. |
| 2013/0280177 A1 | 10/2013 | Raman et al. |
| 2013/0287843 A1 | 10/2013 | Young |
| 2013/0287846 A1 | 10/2013 | Bartholomäus et al. |
| 2013/0320592 A1 | 12/2013 | Arkenau-Maric et al. |
| 2014/0080858 A1 | 3/2014 | Bartholomäus et al. |
| 2014/0080915 A1 | 3/2014 | Bartholomäus et al. |

(Continued)

FOREIGN PATENT DOCUMENTS

| | | |
|---|---|---|
| CA | 3016510 | 9/2017 |
| EP | 1414413 A1 | 5/2004 |

(Continued)

OTHER PUBLICATIONS

International Search Report and Written Opinion for PCT/IB2017/051362 (dated May 12, 2017).
Japanese Application No. 2018547372, filed Sep. 6, 2018, (same application as PCT/IB2017/051362 published as WO2017/153933 on Sep. 14, 2017).
Extended Search Report for European Patent Application No. 17198033.7 (dated Apr. 26, 2018).
"5.17. Recommendations on Methods for Dosage Forms Testing," *European Pharmacapoeia 8.0*, 727-729 (Jan. 2014).
"Guidance for Industry, Dissolution Testing of Immediate Release Solid Oral Dosage Forms," *U.S. Department of Health and Human Services, Food and Drug Administration and Center for Drug Evaluation and Research (CDER)*, 17 page (Aug. 1997).

(Continued)

*Primary Examiner* — Blessing M Fubara
(74) *Attorney, Agent, or Firm* — Klarquist Sparkman, LLP (57) ABSTRACT

The present invention provides immediate release abuse resistant or deterrent formulations such as ingestible dosage form articles suitable for the delivery of one or more medicaments or other active materials.

17 Claims, 2 Drawing Sheets

(56) References Cited

U.S. PATENT DOCUMENTS

| | | |
|---|---|---|
| 2014/0086847 A1 | 3/2014 | Arkenau Maric et al. |
| 2014/0093559 A1 | 4/2014 | Bartholomaeus et al. |
| 2014/0112989 A1 | 4/2014 | Bartholomäus et al. |
| 2014/0147499 A1 | 5/2014 | Bartholomäus et al. |
| 2014/0170079 A1 | 6/2014 | Arkenau Maric et al. |
| 2014/0271835 A1 | 9/2014 | Wengner |
| 2014/0335153 A1 | 11/2014 | Allen et al. |
| 2014/0356294 A1 | 12/2014 | Arkenau-Maric et al. |
| 2014/0378497 A1 | 12/2014 | Myers et al. |
| 2015/0024046 A1 | 1/2015 | Bartholomäus et al. |
| 2015/0031718 A1 | 1/2015 | Wright et al. |
| 2015/0056147 A1 | 2/2015 | Bartholomaeus et al. |
| 2015/0091201 A1 | 4/2015 | Arkenau-Maric et al. |
| 2015/0150812 A1 | 6/2015 | Andersen et al. |
| 2015/0150978 A1 | 6/2015 | Arkenau-Maric et al. |
| 2015/0164811 A1 | 6/2015 | Arkenau-Maric et al. |
| 2015/0182465 A1 | 7/2015 | Arkenau Maric et al. |
| 2015/0216821 A1 | 8/2015 | Bartholomäus et al. |
| 2015/0246005 A1 | 9/2015 | Myers et al. |
| 2015/0250886 A1 | 9/2015 | Bhandari et al. |
| 2015/0283067 A1 | 10/2015 | Kohr |
| 2015/0283086 A1 | 10/2015 | Arkenau-Maric et al. |
| 2015/0313845 A1 | 11/2015 | Bartholomäus et al. |
| 2015/0320690 A1 | 11/2015 | Friedrich et al. |
| 2015/0335592 A1 | 11/2015 | Barnscheid et al. |
| 2016/0000703 A1 | 1/2016 | Micka et al. |
| 2016/0022588 A1 | 1/2016 | Bartholomäus et al. |
| 2016/0058710 A1 | 3/2016 | Arkenau Maric et al. |
| 2016/0106680 A1 | 4/2016 | Bhandari et al. |
| 2016/0113885 A1 | 4/2016 | Myers et al. |
| 2016/0136153 A1 | 5/2016 | Jenkins |
| 2016/0166517 A1 | 6/2016 | Arkenau-Maric et al. |
| 2016/0175256 A1 | 6/2016 | Bartholomäus et al. |
| 2016/0184295 A1 | 6/2016 | Bartholomäus et al. |
| 2016/0263037 A1 | 9/2016 | Arkenau Maric et al. |
| 2016/0279062 A1 | 9/2016 | Rekhi et al. |
| 2016/0310427 A1 | 10/2016 | Wening et al. |
| 2016/0310428 A1 | 10/2016 | Wening et al. |
| 2016/0310437 A1 | 10/2016 | Wening et al. |
| 2016/0310486 A1 | 10/2016 | Wening et al. |
| 2016/0310487 A1 | 10/2016 | Wening et al. |
| 2016/0361306 A1 | 12/2016 | Bartholomaeus et al. |
| 2016/0367484 A1 | 12/2016 | Arkenau-Maric et al. |
| 2016/0367549 A1 | 12/2016 | Bartholomäus et al. |
| 2016/0374963 A1 | 12/2016 | Arkenau-Maric et al. |
| 2017/0216146 A1 | 8/2017 | Hutchison et al. |
| 2019/0029966 A1 | 1/2019 | Young et al. |

FOREIGN PATENT DOCUMENTS

| | | |
|---|---|---|
| EP | 2040685 A2 | 4/2009 |
| EP | 2097069 A1 | 9/2009 |
| EP | 2097070 A1 | 9/2009 |
| EP | 2389169 A1 | 11/2011 |
| EP | 2445487 A2 | 5/2012 |
| EP | 1765298 B1 | 10/2012 |
| EP | 1558257 B1 | 12/2013 |
| EP | 1414418 A1 | 5/2014 |
| EP | 2877161 A1 | 6/2015 |
| EP | 2488161 B1 | 4/2016 |
| EP | 2393487 B1 | 11/2016 |
| EP | 3426234 | 1/2019 |
| EP | 3473246 | 4/2019 |
| JP | 2019507783 | 3/2019 |
| WO | WO2010/083843 | 7/2010 |
| WO | WO2017/153933 | 9/2017 |

OTHER PUBLICATIONS

"Guidance for Industry, Immediate Release Solid Oral Dosage Forms, Scale-Up and Postapproval Changes: Chemistry, Manufacturing, and Controls, In Vitro Dissolution Testing, and In Vivo Bioequivalence Documentation," *Center for Drug Evaluation and Research* (*CDER*), 30 pages (Nov. 1995).

"Reflection paper on the dissolution specification for generic solid oral immediate release products with systemic action," *European Medicines Agency Scient Medicines Health*, 10 pages (Aug. 2017).

Restriction Requirement for U.S. Appl. No. 16/083,364 (dated Sep. 30, 2019).

\* cited by examiner

IMMEDIATE RELEASE ABUSE DETERRENT FORMULATIONS

CROSS REFERENCE TO RELATED APPLICATIONS

This application claims the benefit of European Patent Application No. 17198033.7, fled Oct. 24, 2017, which claims the benefit of European Patent Application No. 17197292.0, filed Oct. 19, 2017, which are hereby incorporated by reference.

PARTIES TO JOINT RESEARCH AGREEMENT

The subject matter disclosed was developed and the claimed invention was made by, on behalf of, and/or in connection with the following parties to a joint research agreement: Alcobra Ltd. and M.W. Encap Limited, a wholly owned subsidiary of Capsugel Belgium NV.

TECHNICAL FIELD

The present disclosure relates to immediate release abuse resistant or deterrent formulations such as ingestible dosage form articles suitable for the delivery of one or more medicaments or other active materials. More particularly, the formulations or dosage form articles are suitable for ingestion by a subject and are resistant or deterrent to abuse, preferably the subject being selected from humans or animals. More particularly, the disclosure relates to orally administrable capsules comprising such immediate release abuse resistant or deterrent formulations. In addition, the present invention relates to a method for preparing abuse deterrent or resistant formulations or dosage form articles.

BACKGROUND

The abuse of pharmaceutical medicaments such as opioids has now become a high profile topic. This abuse often takes the form of extracting, injecting, chewing or snorting different prescription drugs, in contrast to their normal prescribed administration route, in order to increase the effect of the drugs.

A further problem associated with pharmaceutical medicaments is that they can be employed in spiking of drinks in other words so-caged "drug rape" and "drug robbery", etc. Incidents where fast dissolving tablets or powders containing hypnotic type compounds are secretly added to drinks in pubs and clubs have been reported.

It is imperative that manufacturers consider and seriously address the issue of misuse of dosage units.

Some of the most widely used current pharmaceutical medicaments are tablets, powder filled capsules and filled soft gel capsules.

Tablets are a popular way of administering drugs but are open to abuse as they are crushable and the active ingredient can therefore be easily absorbed, extracted, dissolved, ingested or snorted.

Some dosage units are formulated so that they maintain a sustained release profile. Such medicaments contain extremely high doses of active pharmaceutical agent that are released slowly over a long period of time. However, in tablet form this type of dosage unit can be abused by chewing and mixing with saliva, or by crushing, which destroys the sustained release matrix and releases a large dose of the active pharmaceutical agent in a short space of time.

Another popular way of administering pharmaceutical medicaments, which is similar to using tablets, is to use capsules filled with powder. Powder filled capsules can incorporate small amounts of high melting point materials or waxes, but not to any great extent. This is principally due to the method that these capsules are manufactured. In particular, the powder needs to be able to flow such that it can be dispensed by machines when manufacturing the powder filled capsules. Therefore, the powder cannot be made too waxy, gel-like or sticky as it will not flow through the machinery and will not be able to be dispensed properly.

A further method employed for administering pharmaceutical medicaments is to use soft gel capsules that can be manufactured by injecting materials between sheets of wet gelatin. At present, soft gel capsule manufacturing is limited to processing at temperatures of <40° C. and therefore are unsuitable for encasing liquefied high melting point materials. Moreover, the contents of soft gel capsules re-liquefy when heated to 40° C. (which is very close to body temperature) and therefore are easy to extract and inject, making them open to abuse. All types of dosage unit are potentially subject to abuse. However, self-abusers tend to abuse sustained release formulations as these are designed to release drug substances over a prolonged period and thus have a much higher drug loading than dosage units designed for immediate release. Sustained (or prolonged) release formats (normally tablets) do have some inbuilt abuse resistance (as they are specifically designed to release drug substance slowly) but this is overcome immediately by powdering the dosage unit when the drug content can be extracted or absorbed extremely quickly due to the large surface area of the powdered material.

Therefore it would be desirable to mitigate at least some of the problems associated with the prior art. Accordingly, it is an object of the present invention to provide improved abuse resistant formulations and capsules containing such.

SUMMARY

The present invention relates to drug formulation design focusing on the selection of one or more suitable hydrophilic polymeric materials that will swell on contact with water and other solvents such as ethanol typically used for drug extraction from the formulation matrix, hence deterring abuse through injections. In the meantime said formulations should maintain the fast disintegration characteristics required of an immediate release dosage form. Additionally, the selection of one or more carrier materials that enable the final formulations to be homogeneously mixed, uniformly dosed into capsules is performed, since these materials will also impart properties that enable the final dosage form to resist powdering as well as maintaining immediate release characteristics.

The selection of high acyl gellan gum for the formulation of abuse deterrent immediate release formulation unexpectedly led to formulations which not only are more resistant to abuse, but are still easy to process and maintain the required immediate release capabilities.

Many other gum-like hydrophilic polymers have been tested, but none perform equally well. The high acyl gellan gum formulations were tested in combination with several carrier materials and was found to be uniformly applicable with poloxamers, polysorbates, polyethoxylates, polyethylene-glycols, and polyoxyl-glycerides. Preferred but non-limiting examples of such carrier materials are Poloxamer 124, Polysorbate 20, Polysorbate 80, Kolliphor RH40, Kolliphor EL, Polyethylene glycol 6000, Kolliphor HS15, or Gelucire 44/14.

The invention generally provides the following aspects:

Aspect 1: An immediate release, abuse deterrent, pharmaceutical formulation comprising:
an active ingredient formulated in a composition comprising:
from 40-80% w/w based on the total weight of said formulation of a carrier selected from the group comprising: poloxamers, polysorbates, polyethoxylates; polyethyleneglycols; and polyoxyl-glycerides; and
from 20-60% w/w based on the total weight of said formulation of a high acyl gelan gum.

More preferably in said aspect, the active ingredient is formulated in a composition comprising or consisting essentially of:
from 50-80% w/w based on the total weight of said formulation of a carrier selected from the group comprising: poloxamers, polysorbates, polyethoxylates; polyethyleneglycols; and polyoxyl-glycerides; and
from 20-50% w/w based on the total weight of said formulation of a high acyl gellan gum; or
from 55-80% w/w based on the total weight of said formulation of a carrier selected from the group comprising: poloxamers, polysorbates, polyethoxylates; polyethyleneglycols; and polyoxyl-glycerides; and
from 20-45% w/w based on the total weight of said formulation of a high acyl gellan gum; or
from 60-80% w/w based on the total weight of said formulation of a carrier selected from the group comprising: poloxamers, polysorbates, polyethoxylates; polyethyleneglycols; and polyoxyl-glycerides; and
from 20-40% w/w based on the total weight of said formulation of a high acyl gellan gum; or
from 65-80% w/w based on the total weight of said formulation of a carrier selected from the group comprising: poloxamers, polysorbates, polyethoxylates; polyethyleneglycols; and polyoxyl-glycerides; and
from 20-35% w/w based on the total weight of said formulation of a high acyl gellan gum; or
from 55-75% w/w based on the total weight of said formulation of a carrier selected from the group comprising: poloxamers, polysorbates, polyethoxylates; polyethyleneglycols; and polyoxyl-glycerides; and
from 25-45% w/w based on the total weight of said formulation of a high acyl gellan gum; or
from 60-70% w/w based on the total weight of said formulation of a carrier selected from the group comprising: poloxamers, polysorbates, polyethoxylates; polyethyleneglycols; and polyoxyl-glycerides; and
from 30-40% w/w based on the total weight of said formulation of a high acyl gelan gum.

Aspect 2: The formulation according to aspect 1, wherein said composition does not contain a disintegrant, while still maintaining the desired fast disintegrating characteristics.

Aspect 3: The formulation according to aspect 1 or 2, wherein said composition comprises from 50-80% w/w, preferably from 60-80% w/w based on the total weight of said formulation of said carrier.

Aspect 4: The formulation according to aspect 1, 2 or 3, wherein said composition comprises from 20-50% w/w, preferably from 20-40% w/w based on the total weight of said formulation of a high acyl gellan gum.

Aspect 5: The formulation according to any of aspects 1 to 4, wherein said high acyl gellan gum has a weight average molecular weight of at least $5\times10^5$ Daltons, preferably at least $7\times10^5$ Daltons, more preferably at least $1\times10^6$ Daltons, most preferably of between about $1-2\times10^6$ Daltons. The weight average molecular weight of gellan gum can be measured by any method known in the art. Preferably, SEC/MALLS (Size Exclusion Chromatography/Multiple Angle Laser Light Scattering) is used as explained further herein.

Aspect 6: The formulation according to any of aspect 1 to 5, wherein the high acyl gellan gum has a has a set temperature of between 70 and 80° C.

Aspect 7: The formulation according to any of aspects 1 to 6, further comprising at least one other pharmaceutically acceptable excipient.

Aspect 8: The formulation according to any of aspects 1 to 7, wherein at least 70, 75, 80, 85, 90% of the active ingredient is released within 10, 20, 30 or 60 minutes in a USP Apparatus I, II or III in a relevant dissolution medium.

Aspect 9: The formulation according to any of aspects 1 to 8, wherein the active ingredient is an active ingredient susceptible to abuse.

Aspect 10: The formulation according to aspect 9, wherein said active ingredient is selected from the group consisting of: opioids and morphine derivatives; antidepressants; stimulants; halucinogenics; hypnotics; and tranquilizers, amphetamine, alprazolam, codeine, diazepam, fentanyl and analogs thereof, hydrocodone, hydromorphone HCl, lorazepam, meperidine, morphine, methylphenidate, methadone, nitrazepam, oxycodone HCL, oxymorphone, propoxyphene, temazepam, tramadol, zolpidem, and zopiclone.

Aspect 11: The formulation according to any of aspects 1 to 10, wherein the active ingredient is present in an amount ranging from about 0.05% w/w to about 30% w/w based on the total weight of said formulation, preferably from about 0.05% w/w to about 20% w/w, more preferably from about 0.05% w/w to about 5% w/w based on the total weight of said formulation.

Aspect 12: The formulation according to any of aspects 1 to 11, which, when mixed into a solvent, selected from water, hot water, and mixtures of ethanol and water, that is difficult to extract, filter, syringe or inject Aspect 13: The formulation of any of aspects 1 to 12 having a viscosity of greater than 5000 cp.

Aspect 14: A capsule comprising the formulation according to any of aspects 1 to 13, preferably a hard shell capsule, more preferably a gelatin or hydroxypropyl methyl cellulose HPMC hard shell capsule.

DETAILED DESCRIPTION

Development of an immediate release, abuse resistant dosage is often a balancing act. To deter abuse, the API is typically formulated to include a high viscosity polymer, therefore, on reconstitution with water, the dosage form would swell which would either block a syringe, or make injection through the syringe very difficult or impossible. However, a high viscosity polymer that often performs well with deterring syringe ability/injectability, often slows down drug release. Hence, it becomes impossible to achieve the immediate release characteristics required of certain oral dosage forms. In addition, with a very high viscosity formulation, manufacturing may become a significant issue to produce a homogeneous mix and the formulation is difficult to fill consistently into capsules, thereby producing uniform dosage form that is an absolute requirement of medicinal products.

Surprisingly, the incorporation of high acyl gellan gum provides an ideal balance to achieve both the abuse deterrence without compromising the immediate release characteristics.

It is to be understood that the terminology used herein is not intended to be limiting, since the scope of the present invention will be limited only by the appended claims.

As used herein, the singular forms "a", "an", and "the" include both singular and plural referents unless the context dearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any of said members, or to any two or more of said members, such as, e.g., any ≥3, ≥4, 5, ≥6 or ≥7 etc. of said members, and up to all said members.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

The invention hence provides for a pharmaceutical composition comprising:
(a) An active ingredient;
(b) A carrier material that provides fluidity to the composition at ambient or elevated temperatures. Suitable carrier materials include liquid oils such as long and medium chain triglycerides, poloxamers, pehylated fatty acid esters such as various grades of Gelucire, polysorbates, Kolliphors, and polyethylene glycol, or combination thereof; and
(c) A high acyl gellan gum
  The composition is characterized by that
    the composition can be filled into capsules enabled by the fluidity at ambient and elevated temperatures of the carrier material
    the dosage form is disintegrated within 45 min from a modified disintegration testing under the gastric conditions
    the dosage form is resistant to powdering, hence a route of abuse through insufluation
    the dosage form is resistant to dissolution/extraction, hence a route of abuse through injection
    that good uniformity can be attained with the composition The immediate release, abuse deterrent, pharmaceutical formulation preferably comprises: an active ingredient formulated in a composition comprising or consisting essentially of: from 40-80% w/w based on the total weight of said formulation of a carrier selected from the group comprising: poloxamers, polysorbates, polyethoxylates; polyethyleneglycols; and polyoxyl-glycerides; or a combination thereof; and
from 20-60% w/w based on the total weight of said formulation of a high acyl gellan gum.

The formulation according to aspect 1 or 2, wherein said composition comprises from 50-80% w/w, preferably from 60-80% w/w of said carrier based on the total weight of said formulation.

This leads to a formulation comprising from, 0.05-30%, 0.5-20% w/w, preferably 1-15% w/w of active ingredient formulated in said composition.

Figure 1A:
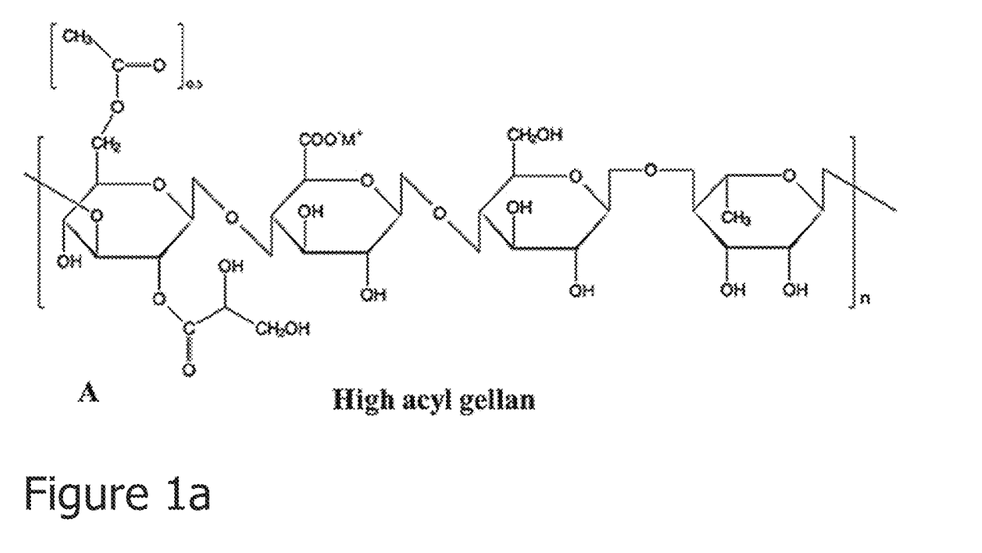
FIGS. 1a and 1b: Structural formula of (A) high- and (B) low-acyl gellan gum.
Figure 1B:
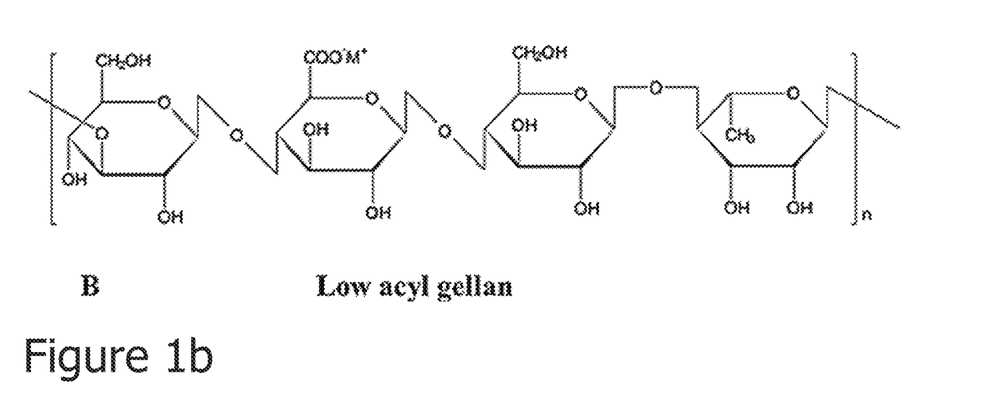

The term "gellan gum" as used herein refers to a hydrocolloid produced by the microorganism *Sphingomonas elodea*. It is manufactured by fermentation of readily available carbohydrate (sugar) stock. Gellan gum is a straight chain polysaccharide based on the repeating units of glucose, rhamonose and glucuronic units. In its native form, gellan gum has two acyl substituents-acetate and glycerates, and on average there is one glycerate per repeat and one acetate per every two repeats (cf. FIG. 1a). Frequently the material produced from fermentation is further processed through alkali treatment, as a result, the acyl substituents (acetate and glycerate groups) are removed. This is often referred to as low acyl gellan gum (cf. FIG. 1b), while the native gum is referred to as high acyl gellan gum.

The term "high acyl gellan gum" hence refers to the native gellan gum, i.e., the gellan gum still having its two acyl substituents. The high acyl gellan gum has a typical weight average molecular weight of at least $5 \times 10^8$ Daltons, preferably of at least $7 \times 10^5$ Daltons, more preferably of at least $1 \times 10^6$ Daltons, most preferably of between about $1-2 \times 10^6$ Daltons. Low acyl gellan gun has a much lower weight average molecular weight of below $5 \times 10^6$ Daltons, preferably of about $2-3 \times 10^6$ Daltons. The molecular weight of gellan gum can be measured by any method known in the art. Preferably, SEC/MALLS (Size Exclusion Chromatography/Multiple Angle Laser Light Scattering) is used as explained further herein.

The high acyl gellan gum has a set temperature of 70-80° C. and low acyl gellan gum a temperature of 30-50° C. Low acyl gellan gum can form firm, non-elastic and brittle gels while high acyl gellan gum forms soft and elastic gels. High acyl gellan gum is commercially available. Particular, but non-limiting examples are the high acyl gellan gum marketed by CP Kelco as KelcogeP CGHA™ or Kelcoge® LT100.

In order to determine the molecular weight of gellan gum in general, any known method in the art can be used. Preferably however Size Exclusion Chromatography/Multiple Angle Laser Light Scattering is used as disclosed in U.S. Pat. No. 6,242,035 from CP Kelco US. The procedure described in said patent is repeated below:
  Native gellan broth was clarified as follows: to approximately 4 liters of a 1.5% gellan gum broth solution was added sufficient sodium hydochloride to yield a solution having a sodium hydochloride concentration of 1000 ppm. The solution was stirred for 2 hours at 40° C., followed by addition of sufficient Lysozyme (Genencor, Palo Alto, Calif.) to yield a solution having a Lysozyme concentration of 50 ppm. The resultant solution was stirred for 2 hours at 40° C., followed by addition of sufficient HT Protease (Miles Enzymes, Elkhart, Ind.) to yield a solution having an HT Protease concentration of 500 ppm. The resultant solution was stirred for 2 hours at 40° C., followed by addition of sufficient ethylenediaminetetraacetate (EDTA) and sodium dodecyl sulphate (SDS) to yield a solution having EDTA and SDS concentrations of 1000 ppm and 500 ppm, respectively. The resultant solution was stirred for 2 hours at 40° C. The resultant clarified native gellan broth was then precipitated with two parts by volume isopropyl alcohol. The precipitated gum fiber was then pressed between muslin cloth to 33% solids, and then dried at 60° C. for 12 hours. The fiber was then milled to approximately 250 μm particle size using a Brinkmann knife mill (Westbury, N.Y.). The dried powder gum was then rehydrated to 1% polymer concentration in deionized water at 90° C.

The 1% solution of native gellan gum then was added to a molecular porous dialysis tubing (Spectra/Port Membrane MWCO 6-8000). The solution was dialyzed against deionized water for 72 hours. The dialyzed gellan gum was precipitated with isopropyl alcohol before being dried and milled. The polymer was then rehydrated in deionized water to 0.05% polymer concentration at 90° C. Tetramethylammonium chloride (TMAC) was added to yield a 10 mM solution. This purification process was repeated. The resultant solution was cooled to room temperature.

The polymer solution was filtered through both 0.45 μm and 0.50 μm Acrodisc filters. The molecular weight of the native gellan gum polymer was measured using a SEC/MALLS (Size Exclusion Chromatography/Multiple Angle Laser Light Scattering) unit. The SEC/MALLS unit was fitted with a water 410 differential refractometer, a Wyatt Technology-Dawn DSP laser photometer and two Waters Hydrogel columns (2000 and linear in series). Native gellan gum typically has a weight average molecular weight (Mw) and a number average molecular weight (Mn) of $2.5 \times 10^6$ and $2.2 \times 10^6$, respectively when using said measurement method.

Note that the "number average molecular weight" or "Mn" is the total weight of the sample divided by the number of molecules in said sample, while the "weight average molecular weight" or "Mw" is the sum of the weight of the different molecules in the sample calculated on their respective weight fractions in the sample.

The term "does not contain a disintegrant" as used herein needs to be interpreted as comprising less than about 0.9% disintegrant, preferably less than about 0.8%, less than about 0.7% disintegrant, less than about 0.6% disintegrant, less than about 0.5% disintegrant, less than about 0.4% disintegrant, less than about 0.3% disintegrant, less than about 0.2% disintegrant, or less than about 0.1% disintegrant is present in the composition referred to. Since one cannot achieve a 100% purity in formulating compositions, the term "does not contain a disintegrant" in essence is used to indicate that no disintegrant has been actively added to the composition, i.e., such as to exert a disintegration effect on said composition.

The term "disintegrant" as used herein encompasses all agents that have the effect of disintegrating a drug formulation upon administration, thereby increasing the bioavailability and immediate release characteristics of the formulation. Typical but non-limiting examples of disintegrants are: crosslinked polymers such as crosslinked polyvinylpyrrolidone (crospovidone) and crosslinked sodium carboxymethyl cellulose (croscarmellose sodium), sodium starch glycolate, sodium pregelatinized starch, modified corn starch or combinations thereof.

The term "carrier" as used herein encompasses (co-) polymers such as those selected from the group comprising: triglycerides, poloxamers, polysorbates, polyethoxylates, polyethylene-glycols, and polyoxyl-glycerides. Preferred but non-limiting examples of such carrier materials are Poloxamer 124, Polysorbate 20, Polysorbate 80, Koliphor RH40, Koliphor EL, Polyethylene glycol 1000, 1500, 2000, 6000 and 8000, Kolliphor HS15, or Gelucire 44/14, Gelucire 48/16, Gelucire 50/13.

The term "susceptible for abuse" when referred herein for active ingredients, pharmaceutical compositions, or drugs means that such active ingredients are known to have properties that can lead to addiction. In general in includes all actives being capable of creating a high of some sort, or actives that can cause psychological and/or physical dependence on the active. Some examples are pain-killers, analgesics, sleeping pills, anti-anxiety medication, sedatives, sedative-hypnotics, hallucinogenics, tranquilizers, stimulants, anti-depressants, narcolepsy treating actives, attention-deficit treating actives ADHD-treating actives, or psychoactive drugs. Non-limiting examples are: opioids, amphetamines, alfentanil, alprazolam, allylprodine, alphaprodine, amphetamine, anileridine, benzylmorphine, bezitramide, buprenorphine, butorphand, clonitazene, codeine, cyclazocine, desomorphine, dextromoramide, dezocine, diampromide, diazepam, dihydrocodeine, dihydroetorphine, dihydromorphine, dimenoxadol, dimepheptanol, dimethylthiambutene, dioxaphetyl butyrate, dipipanone, eptazocine, ethoheptazine, ethylmethyithiambutene, ethylmorphine, etonitazene etorphine, fentanyl, heroin, hydrocodone, hydromorphone, hydroxypethidine, isomethadone, ketobemidone, levallorphan, levorphanol, lofentanil, levophenacylmorphan, lorazepam, meperidine, meptazinol, metazocine, methadone, methylphenidate, metopon, morphine, myrophine, nalbuphine, narceine, nicomorphine, nitrazepam, nitrozepam, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, temazepam, tramadol, tilidine, zolpidem, zopiclone, pharmaceutically acceptable salts thereof and prodrugs thereof.

Typically, a particular dose of an active is more potent when administered parenterally when compared to the same dose administered orally via the oral mucosa or the gastrointestinal tract, which can trigger addicts to try to mix the original formulation with solvents such as e.g., water or ethanol in order to e.g., inject the active directly rather than taking it orally. Alternatively, grinding or crushing the formulation comprising the active into a fine powder which can be inhaled or snorted can lead to abuse.

The term "abuse resistant" or "abuse deterrent" implies any formulation that is designed in such a manner that the extraction of active ingredients is hindered, the bioavailability of actives through product manipulation is decreased, the onset of action delayed and/or the administration of the active through alternative routes is hindered or prevented. Exemplary characteristics encompass high viscosity substantially rendering the formulation uninjectable, even when the formulation is mixed with (heated) water or organic solvents such as alcohol. Typically, viscosity increases upon heating the formulation in water or organic solvents such as alcohol. Upon exposure to water or another liquid, the viscosity of the mixture increases to such a level that it is difficult or impossible to fill an insulin syringe with the mixture. In another embodiment, the viscosity of the heated mixture increases to the level that it may not be deliverable even through needles with the largest diameters e.g., commonly used in delivery of insulin.

The term "uninjectable" or "unsuitable for Injection" as used herein implies that one would have substantial difficulty manipulating the tampered dosage form with the goal of injecting it with the use of a syringe. The main reasons which would justify a tampered dosage form to be unsuitable for injection are the following: due to pain upon administration or difficulty of pulling the drug into the syringe and/or pushing the dosage form through a syringe.

The present invention is further illustrated in the following non-limiting examples.

EXAMPLES

Example 1: Formulation Design

Materials and Methods
Sample Preparation:

Placebo formulations were prepared on a 20 g scale, the carrier material is blended with the selected hydrophilic polymer(s) to achieve a uniform mix. Certain carrier materials that are solid or semi-solid at room temperature, were molten prior to being combined with the polymers. The mixes were then subsequently filled into gelatin hard capsules (size 0, approximately 500 mg).

The following carrier materials were evaluated:
Poloxamer 124
Polysorbate 20
Polysorbate 80
Kolliphor RH40
Kolliphor EL
Polyethylene glycol 6000
Kolliphor HS15
Gelucire 44/14

The following hydrophilic polymers were evaluated:
Guar gum
Xanthan gum
High acyl gellan gum
Low acyl gellan gum
Carboxymethyl cellulose
Povidone
Sodium alginate The formulations were assessed based on three main selection criteria:

Process-ability: this was assessed on whether high shear mixing was required, if it was, then how effective it was, to prepare the formulation; the propensity for phase separation; the presence of air bubbles in the mix and how easy it was to de-gas under vacuum. This was ranked between a scale of 1 to 4 with 1, representing excellent, 2, acceptable, 3, poor and 4, impossible.

Disintegration testing: a modified USP disintegration test method was employed to test the disintegration rate of the placebo capsules using 0.1M HCl simulating gastric conditions, hence providing an indication of the likely drug release characteristics.

Syringeability/Injectability assessment the dose unit was reconstituted in either 2 ml, 4 ml and 6 ml cold, warm water (60° C.) or 40% ethanol solution. The reconstituted mixture was either drawn through a 26 gauge needle, or a 5 ml syringe with the needle removed. The drawn mixture was then attempted to expel through a 26 gauge needle through a plunger. The difficulty of expelling through the syringes were ranked between a scale of 1 to 4 with 1, representing excellent when the diluted formulation was not possible to inject or very slowly, 2, acceptable, difficult to inject, initial drop wise flow; 3, poor, moderate flow and 4, easy continuous flow/injection.

Results

The results are outlined in the tables on the following pages, wherein a score is given for the three characteristics measured: process-ability, disintegration rate and syringeability as indicated above.

TABLE 1

Formulations comprising Guar Gum

| Batch | Formulation Composition | Processability | Disintegration | Syringeability Water 2 ml | 4 ml | 6 ml | Warm Water 2 ml | 4 ml | 6 ml | Ethanol 2 ml | 4 ml | 6 ml |
|---|---|---|---|---|---|---|---|---|---|---|---|---|
| 0623/12/01 | 30% GG 70% Tween 20 | 4 | 3 mins | 4 | — | — | — | — | — | — | — | — |
| 0623/13/01 | 30% GG 70% Tween 80 | 4 | INCOMPLETE | 4 | — | — | — | — | — | — | — | — |
| 0623/14/01 | 30% GG 70% Kolliphor RH40 | 2 | 50 mins | 3 | — | — | 3 | — | — | — | — | — |
| 0623/17/01 | 30% GG 70% Kolliphor EL | 4 | INCOMPLETE | 3 | — | — | — | — | — | — | — | — |
| 0623/18/01 | 30% GG 70% Gelucire 44/14 | 2 | INCOMPLETE | 2 | 3 | 4 | — | — | — | — | — | — |
| 0623/37/02 | 50% GG 50% Tween 80 | 4 | INCOMPLETE | 4 | — | — | 3 | — | — | — | — | — |

TABLE 1-continued

Formulations comprising Guar Gum

| Batch | Formulation Composition | Processability | Disintegration | Syringeability Water 2 ml | 4 ml | 6 ml | Warm Water 2 ml | 4 ml | 6 ml | Ethanol 2 ml | 4 ml | 6 ml |
|---|---|---|---|---|---|---|---|---|---|---|---|---|
| 0623/37/04 | 50% GG 50% PEG6000 | 4 | 40 mins | 4 | — | — | 3 | — | — | — | — | — |
| 0623/37/07 | 50% GG 50% Gelucire 44/14 | 4 | INCOMPLETE | — | 4 | — | — | — | — | — | — | — |
| 0623/41/01 | 50% GG 50% Tween 20 | 4 | 10 mins | 4 | — | — | — | — | — | — | — | — |
| 0623/43/01 | 50% GG 50% Kolliphor EL | 1 | INCOMPLETE | 3 | — | — | — | — | — | — | — | — |
| 0623/44/01 | 50% GG 50% Kolliphor RH40 | 1 | INCOMPLETE | 3 | — | — | — | — | — | — | — | — |
| 0623/45/01 | 50% GG 50% Kolliphor HS15 | 4 | INCOMPLETE | 4 | — | — | — | — | — | — | — | — |
| 0623/68/01 | 50% GG 50% Poloxamer 124 (Reference) | 1 | 25 mins | 4 | 4 | — | 4 | 4 | — | 3 | 3 | — |
| 0623/75/01 | 47.5% GG 47.5% Kolliphor EL 5% Polyplasdone XL | 4 | INCOMPLETE | 1 | 2 | — | 1 | 3 | — | — | 4 | — |
| 0623/75/02 | 47.5% GG 47.5% Kolliphor EL 5% Explotab | 1 | INCOMPLETE | 1 | 3 | — | 3 | — | — | 3 | 4 | — |
| 0623/75/03 | 47.5% GG 47.5% Gelucire 44/14 5% Polyplasdone XL | 4 | INCOMPLETE | 1 | 3 | — | 1 | 3 | — | 4 | 4 | — |
| 0623/75/04 | 47.5% GG 47.5% Gelucire 44/14 5% Explotab | 1 | INCOMPLETE | 1 | 2 | — | 1 | 2 | — | 2 | 4 | — |
| 0623/75/05 | 47.5% GG 47.5% Kolliphor RH40 5% Polyplasdone XL | 4 | INCOMPLETE | — | — | — | — | 4 | — | 3 | 2 | 2 |
| 0623/75/06 | 47.5% GG 47.5% Kolliphor RH40 5% Explotab | 2 | INCOMPLETE | 1 | 3 | — | 2 | 3 | — | 4 | 4 | — |
| 0623/75/07 | 47.5% GG 47.5% PEG6000 5% Polyplasdone XL | 2 | 50 mins | 3 | — | — | — | — | — | 4 | — | — |
| 0623/75/08 | 47.5% GG 47.5% PEG6000 5% Explotab | 2 | 45 mins | 4 | — | — | 4 | — | 3 | — | — |

TABLE 1-continued

Formulations comprising Guar Gum

| Batch | Formulation Composition | Processability | Disintegration | Syringeability Water 2 ml | 4 ml | 6 ml | Warm Water 2 ml | 4 ml | 6 ml | Ethanol 2 ml | 4 ml | 6 ml |
|---|---|---|---|---|---|---|---|---|---|---|---|---|
| 0623/75/09 | 47.5% GG 47.5% Poloxamer 124 5% Polyplasdone XL | 1 | 8 mins | 4 | 4 | — | 4 | 4 | — | 4 | 4 | — |
| 0623/75/10 | 47.5% GG 47.5% Poloxamer 124 5% Explotab | 1 | 14 mins | 4 | 4 | — | 4 | 4 | — | 2 | 4 | — |
| 0623/88/01 | 30% GG 60% Gelucire 44/14 10% Polyplasdone XL | 4 | INCOMPLETE | 1 | 2 | — | 1 | 2 | — | 4 | 2 | — |
| 0623/88/02 | 40% GG 50% Gelucire 44/14 10% Polyplasdone XL | 4 | INCOMPLETE | 1 | 1 | — | 2 | 2 | — | 4 | 3 | — |
| 0623/88/03 | 30% GG 60% Kolliphor RH40 10% Polyplasdone XL | 4 | 60 mins | 2 | 3 | — | 3 | 3 | — | 4 | 4 | — |
| 0623/88/04 | 40% GG 50% Kolliphor RH40 10% Polyplasdone XL | 4 | INCOMPLETE | 1 | 3 | — | 1 | 3 | — | 3 | 4 | — |

Despite of the very extensive development work with various ratios and in combination with a large variety of the excipients, the data shows that overall, guar gum is not a suitable candidate for the formulation of an immediate abuse deterrent drug products.

Polyplasdone™ and Explotab™ are commonly used as super-disintegrants for oral solid dosage forms. They were included in some of the formulations to improve disintegration characteristics and to impede syringeability as they enhance disintegration through the hydration of the water insoluble but swellable particles. Yet, no formulation was obtained that scored at least good for all three characteristics.

TABLE 2

Formulations comprising Xanthan Gum (Xantural 75 ™)

| | | | | Water 2 ml | 4 ml | 6 ml | Warm Water 2 ml | 4 ml | 6 ml | Ethanol 2 ml | 4 ml | 6 ml |
|---|---|---|---|---|---|---|---|---|---|---|---|---|
| 0623/96/01 | 50% Xantural 75 50% Kolliphor RH40 | 1 | INCOMPLETE | 1 | 1 | 3 | 1 | 3 | 2 | 1 | 1 | 2 |
| 0623/96/02 | 50% Xantural 75 50% Gelucire 44/14 | 1 | INCOMPLETE | 1 | 1 | 1 | 1 | 2 | 3 | 1 | 2 | 2 |
| 0623/96/03 | 30% Xantural 11K 70% Kolliphor RH40 | 4 | — | — | — | — | — | — | — | — | — | — |

TABLE 2-continued

Formulations comprising Xanthan Gum (Xantural 75 ™)

| | | | | Water | | | Warm Water | | | Ethanol | | |
|---|---|---|---|---|---|---|---|---|---|---|---|---|
| | | | | 2 ml | 4 ml | 6 ml | 2 ml | 4 ml | 6 ml | 2 ml | 4 ml | 6 ml |
| 0623/96/04 | 30% Xantural 11K 70% Gelucire 44/14 | 4 | — | — | — | — | — | — | — | — | — | — |
| 0623/104/01 | 50% Xantural 75 50% Kolliphor EL | 1 | INCOMPLETE | 1 | 1 | 3 | 1 | 3 | 3 | 1 | 1 | 3 |
| 0623/104/02 | 50% Xantural 75 30% Kolliphor RH40 20% Miglyol | 1 | INCOMPLETE | 1 | 1 | 3 | 2 | 3 | 3 | 1 | 1 | 2 |
| 0623/104/03 | 40% Xantural 75 30% Kolliphor RH40 30% PEG6000 | 1 | 50 mins | 1 | 2 | 3 | 2 | 2 | 3 | 1 | 2 | 3 |
| 0623/144/01 | 20% Kolliphor RH40 40% Xantural 75 40% PEG6000 | 1 | 60 mins | 1 | 3 | 4 | 1 | 3 | 4 | 1 | 3 | 3 |
| 0623/147/01 | 20% Gelucire 44/14 40% Xantural 75 40% PEG6000 | 1 | 31 mins | 2 | 3 | 4 | 2 | 3 | 4 | 1 | 1 | 3 |

The data shows that overall, xanthan gum is not a suitable candidate for the formulation of an immediate abuse deterrent drug products.

TABLE 3

Formulations comprising Povidone (Kollidon 90F ™)

| | | | | Water | | | Warm Water | | | Ethanol | | |
|---|---|---|---|---|---|---|---|---|---|---|---|---|
| | | | | 2 ml | 4 ml | 6 ml | 2 ml | 4 ml | 6 ml | 2 ml | 4 ml | 6 ml |
| 0623/123/01 | 40% Kelocogel CGLA 60% Kolliphor RH40 | 4 | — | — | — | — | — | — | — | — | — | — |
| 0623/123/02 | 30% Kollidon 90F 70% Gelucire 44/14 | 4 | — | — | — | — | — | — | — | — | — | — |
| 0623/123/03 | 30% Kollidon 90F 70% Kolliphor RH40 | 1 | 80 mins | 3 | 4 | 4 | 3 | 4 | 4 | 3 | 4 | 4 |

The data shows that overall, povidone (PVP) is not a suitable candidate for the formulation of an immediate abuse deterrent drug products.

TABLE 4

Formulations comprising Carboxymethyl cellulose

|  |  |  | | Water | | | Warm Water | | | Ethanol | |
|---|---|---|---|---|---|---|---|---|---|---|---|
|  |  |  | 2 ml | 4 ml | 6 ml | 2 ml | 4 ml | 6 ml | 2 ml | 4 ml | 6 ml |
| 0623/131/01 | 50% CMC 7H4XF 50% Kolliphor RH40 | 4 | — | — | — | — | — | — | — | — | — |
| 0623/131/02 | 50% CMC 7M31F 50% Kolliphor RH40 | 4 | — | — | — | — | — | — | — | — | — |
| 0623/131/03 | 40% CMC 7H3SF 60% Kolliphor RH40 | 1 | INCOMPLETE | 1 | 2 | 3 | 1 | 2 | 3 | 1 | 2 | 1 |
| 0623/133/01 | 40% CMC 7H4XF 60% Gelucire 44/14 | 2 | 95 mins | 1 | 2 | 3 | 1 | 2 | 3 | 1 | 1 | 1 |
| 0623/133/02 | 40% CMC 7M31F 60% Gelucire 44/14 | 4 | — | — | — | — | — | — | — | — | — |
| 0623/133/03 | 40% CMC 7H3SF 60% Gelucire 44/14 | 1 | 52 mins | 1 | 2 | 3 | 1 | 2 | 4 | 1 | 1 | 2 |
| 0623/163/03 | 30% CMC 7H3SF 70% PEG6000 | 1 | 52 mins | 1 | 2 | 3 | 1 | 2 | 1 | | | |
| 0623/163/04 | 50% CMC 7H3SF 50% PEG6000 | 4 | — | | | | | | | | | |

The data shows that overall, CMC is not a suitable candidate for the formulation of an immediate abuse deterrent drug products.

TABLE 5

Formulations comprising sodium alginate

|  |  |  | | Water | | | Warm Water | | | Ethanol | |
|---|---|---|---|---|---|---|---|---|---|---|---|
|  |  |  | 2 ml | 4 ml | 6 ml | 2 ml | 4 ml | 6 ml | 2 ml | 4 ml | 6 ml |
| 0623/165/03 | 50% Gelucire 44/14 50% Kimica Algin | 1 | INCOMPLETE | | | | | | | | | |
| 0623/165/04 | 50% Kolliphor RH40 50% Kimica Algin | 1 | INCOMPLETE | 1 | 2 | 3 | 1 | 2 | 3 | 1 | 3 | 4 |
| 0623/165/01 | 50% Gelucire 44/14 50% Protanal CR8223 | 1 | INCOMPLETE | 1 | 2 | 3 | 1 | 1 | 3 | | 4 | 4 |
| 0623/165/02 | 50% Kolliphor RH40 50% Protanal CR8223 | 1 | INCOMPLETE | 1 | 2 | 3 | 1 | 1 | 3 | 4 | 4 | 4 |

The data shows that overall, sodium alginate is not a suitable candidate for the formulation of an immediate abuse deterrent drug products.

TABLE 6

Formulations comprising High Acyl Gellan Gum (Kelcogel CGHA ™)

|  |  |  |  | Water | | | Warm Water | | | Ethanol | | |
|---|---|---|---|---|---|---|---|---|---|---|---|---|
|  |  |  |  | 2 ml | 4 ml | 6 ml | 2 ml | 4 ml | 6 ml | 2 ml | 4 ml | 6 ml |
| 0623/99/03 | 40% Kelcogel CGHA 60% Kolliphor RH40 | 1 | 50 mins | 1 | 1 | 1 | 1 | 1 | 2 | 2 | 2 | 2 |
| 0623/99/04 | 30% Kelcogel CGHA 70% Gelucire 44/14 | 1 | 50 mins | 1 | 1 | 1 | 1 | 1 | 1 | 1 | 1 | 1 |
| 0623/144/03 | 33% Kolliphor RH40 33% Kelcogel CGHA 33% PEG6000 | 2 | 52 mins |  | 1 |  |  | 1 |  |  | 2 |  |
| 0623/147/03 | 33% Gelucire 44/14 33% Kelcogel CGHA 33% PEG6000 | 2 | 70 mins |  | 1 |  |  | 1 |  |  | 2 |  |
| 0623/163/01 | 30% Kelcogel CGHA 70% PEG6000 | 1 | 27 mins | 1 | 1 | 1 |  | 1 | 1 | 1 | 1 | 1 |
| 0623/167/02 | 70% Poloxamer 124 30% Kelcogel CGHA | 1 | 10 mins | 1 | 1 | 1 | 1 | 1 | 1 | 1 | 1 | 1 |
| 0623/174/02 | 60% Kolliphor RH40 40% Kelcogel CGHA | 1 | 25 mins | 1 | 1 | 1 | 1 | 1 | 1 | 1 | 1 | 1 |
| 0623/182/01 | 70% Tween 20 30% Kelcogel CGHA | 1 | 11 mins | 1 | 1 | 1 | 1 | 1 | 1 | 1 | 1 | 2 |
| 0623/182/02 | 70% Tween 80 30% Kelcogel CGHA | 1 | 22 mins | 1 | 1 | 1 | 1 | 1 | 1 | 1 | 1 | 2 |
| 0623/182/03 | 70% Kolliphor HS15 30% Kelcogel CGHA | 1 | 22 mins | 1 | 1 | 1 | 1 | 1 | 1 | 1 | 2 | 1 |
| 0623/182/04 | 70% Kolliphor EL 30% Kelcogel CGHA | 1 | 30 mins | 1 | 1 | 1 | 1 | 1 | 1 | 1 | 1 | 1 |

The data shows that high acyl gellan gum is an excellent candidate for the formulation of an immediate release abuse deterrent dosage form. To illustrate the effect of the optimal concentration range, different amounts of high acyl gellan gum was incorporated (see Table 7 below). This shows that no less than 20% of gellan gum should be incorporated in the formulations.

TABLE 7

Comparison with different amounts of high acyl gellan gum

|  |  |  |  | Water | | | Warm Water | | | Ethanol | | |
|---|---|---|---|---|---|---|---|---|---|---|---|---|
|  |  |  |  | 2 ml | 4 ml | 6 ml | 2 ml | 4 ml | 6 ml | 2 ml | 4 ml | 6 ml |
| 0623/189/01 | 75% Kolliphor RH40 25% Kelcogel CGHA | 1 | 20 mins | 1 | 1 | 2 | 1 | 1 | 1 | 1 | 1 | 1 |
| 0623/189/02 | 80% Kolliphor RH40 20% Kelcogel CGHA | 1 | 20 mins | 1 | 1 | 2 | 1 | 1 | 2 | 1 | 1 | 1 |

TABLE 7-continued

Comparison with different amounts of high acyl gellan gum

| | | | | Water | | | Warm Water | | | Ethanol | | |
|---|---|---|---|---|---|---|---|---|---|---|---|---|
| | | | | 2 ml | 4 ml | 6 ml | 2 ml | 4 ml | 6 ml | 2 ml | 4 ml | 6 ml |
| 0623/189/03 | 85% Kolliphor RH40 15% Kelcogel CGHA | 1 | 18 mins | 1 | 2 | 3 | 1 | 2 | 3 | 1 | 1 | 3 |
| 0623/189/04 | 90% Kolliphor RH40 10% Kelcogel CGHA | 1 | 15 mins | 1 | 3 | 4 | 1 | 3 | 4 | 1 | 3 | 4 |

TABLE 8

Formulations comprising Low Acyl Gellan Gum (Kelcogel CGLA ™)

| | | | | Water | | | Warm Water | | | Ethanol | | |
|---|---|---|---|---|---|---|---|---|---|---|---|---|
| | | | | 2 ml | 4 ml | 6 ml | 2 ml | 4 ml | 6 ml | 2 ml | 4 ml | 6 ml |
| 0623/174/01 | 60% Kolliphor RH40 40% Kelcogel CGLA | 1 | 25 mins | 2 | 2 | 3 | 1 | 3 | 3 | 1 | 4 | 4 |
| 0623/99/02 | 40% Kelcogel CGLA 60% Gelucire 44/14 | 1 | 50 mins | 1 | 1 | 2 | 1 | 3 | 3 | 1 | 1 | 1 |

The data shows that low acyl gellan gum is inferior to high acyl gellan gum in the formulation of an immediate release abuse deterrent dosage form.

CONCLUSIONS

To conclude, the above depicted results clearly indicate that the use of at least about 20% high-acyl Gellan Gum improves the abuse deterrent characteristics of the dosage forms, while maintaining the required processability and disintegration time, indicative of immediate release capability.

Example 2: Prototype Placebo Formulation Development

To further evaluate the utility of the prototype placebo formulations, a series of 'mock' active formulations using caffeine as a mock active at 1.74% (based on 100% excipients) were prepared at a larger scale, these formulations were then filled into capsules using a semi-automated filling machine to assess the scale-ability and performance of these formulations. The results are in Table 9.

Formulation Manufacture

The required mass of carrier excipient was weighed into an appropriately sized beaker. To this was then added the appropriate quantity of hydrophilic polymeric material. This was manually mixed until thoroughly wetted. Caffeine was then added and manually mixed for approximately 5 minutes to attain an even distribution and to wet the compound. The resulting mixture was then high sheared until visually homogenous. The same high shearer, high shear head and method of mixing was the same for all formulations; except the first one made, where a different head was used which significantly affected the homogenization process time.

Filling Process

The filling process using semi-automatic Hi bar appears to straight forward for the majority of formulations. A few formulations could be filled at ambient temperature; and after an initial fill-temperature assessment (with a thermo-softening formulation) the other formulations were filled in line with the excipients' melting points.

All banded capsules were leak tested—there was no leaking capsule across all 12 batches.

Disintegration Testing

Disintegration of the scale-up batches was tested to determine if they were in line with what had been seen with the lead formulations. The data was largely in agreement with what was seen at the smaller scale.

The overall performance of these formulations is summarised in Table 9.

TABLE 9

Disintegration time of different formulations

| Batch | Formulation Composition | Scale-up Formulations | Placebo Formulations | Notes |
|---|---|---|---|---|
| 0623/163/01 1043/05/01 | 30% Kelcogel CGHA 70% PEG6000 | 32 mins | 27 mins | |
| 0623/167/02 1043/05/02 | 70% Poloxamer 124 30% Kelcogel CGHA | 10 mins | 10 mins | |
| 0623/99/04 1043/06/01 | 30% Kelcogel CGHA 70% Gelucire 44/14 | 55 mins | 50 mins | |
| 0623/99/03 1043/06/02 | 40% Kelcogel CGHA 60% Kolliphor RH40 | 30 mins | 50 mins | 64% Kolliphor in scale up |
| 0623/99/02 1043/06/03 | 40% Kelcogel CGLA 60% Gelucire 44/14 | 55 mins | 50 mins | |
| 0623/133/03 1043/06/04 | 40% CMC 7H3SF 60% Gelucire 44/14 | 75 mins | 52 mins | |
| 0623/104/03 1043/06/05 | 40% Xantural 75 30% Kolliphor RH40 30% PEG6000 | 57 mins | 50 mins | |
| 0623/147/01 1043/06/06 | 20% Gelucire 44/14 40% Xantural 75 40% PEG6000 | 30 mins | 31 mins | |
| 0623/182/01 1043/07/01 1043/22/01 | 70% Tween 20 30% Kelcogel CGHA | 10 mins | 11 mins | |
| 0623/182/02 1043/07/02 | 70% Tween 80 30% Kelcogel CGHA | 20 mins | 22 mins | |

Dissolution Performance

Though disintegration testing often provides excellent indicative data on drug release, the definition of an immediate release dosage depends on the in-vitro release performance of the active. These formulations were subjected to dissolution testing based ion modified USP method to assess the release of caffeine from these capsules.

Figure 2:
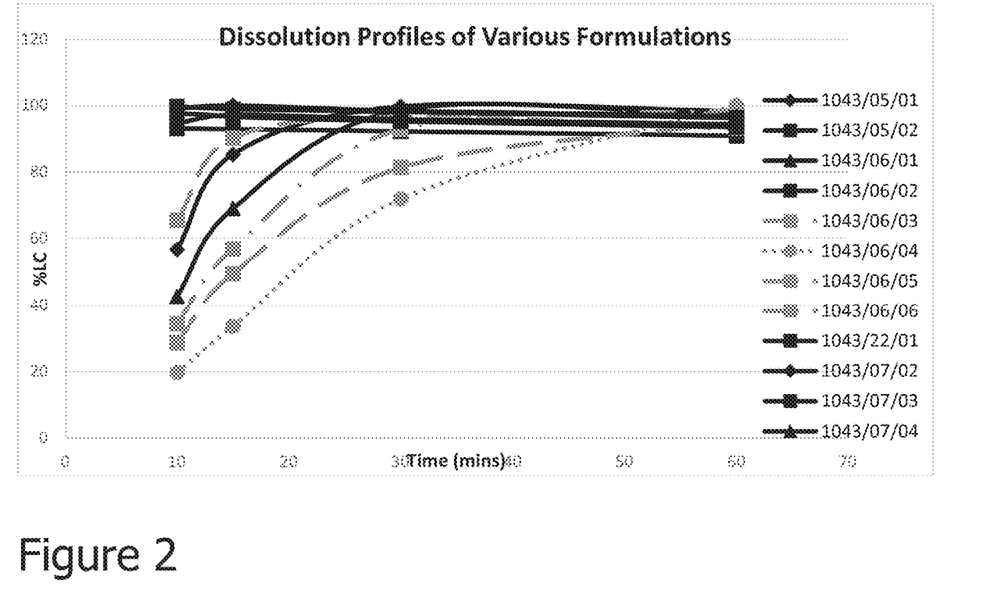
FIG. 2: Dissolution tests of different formulations to assess the release of caffeine from capsules comprising said respective formulations.

The data further confirms that the high acyl gellan gum based formulation provides consistent and fast release profiles that are significantly less dependent on the carrier materials. The results are depicted in FIG. 2.

The solid lines representing high acyl gellan gum based formulations are denoted as: 1043/05/01; 1043/05/02; 1043/06/01; 1043/06/02; 10432/22/01; 1043/07/02; and 1043/07/03 (cf. Table 9 for their actual compositions).

The broken lines representing xanthan gum based formulations are denoted as: 1043/06/05 and 1043/06/06, (scale up of 0623/104/03 and 0623/147/01 respectively, cf. Table 2 for their actual compositions).

The dashed/dotted line representing a low acyl gellan gum based composition is denoted as: 1043/06/03 (scale up of 0623/99/02 cf. Table 8 for the actual composition).

The dotted line representing a CMC based formulation is denoted as: 1043/06/04 (scale up of 0623/133/03, cf. Table 4 for the actual composition).

The invention claimed is:

1. An immediate release, abuse deterrent, pharmaceutical formulation comprising:
    an active ingredient formulated in a composition comprising:
    from 40-80% w/w based on the total weight of the formulation of a carrier selected from the group comprising: poloxamers, polysorbates, polyethoxylates; polyethylene-glycols; and polyoxyl-glycerides; and combination thereof; and
    from 20-60% w/w based on the total weight of the formulation of a high acyl gellan gum, where the composition does not contain a disintegrant.

2. The formulation according to claim 1, wherein the composition comprises from 50-80% w/w based on the total weight of the formulation of the carrier.

3. The formulation according to claim 1, wherein the composition comprises from 20-50% w/w based on the total weight of the formulation of a high acyl gellan gum.

4. The formulation according to claim 1, wherein the high acyl gellan gum has a weight average molecular weight of at least $5 \times 10^5$ Daltons.

5. The formulation according to claim 1, wherein the high acyl gellan gum has a set temperature of between 70 and 80° C.

6. The formulation according to claim 1, further comprising at least one other pharmaceutically acceptable excipient.

7. The formulation according to claim 1, wherein the active ingredient is an opioid and at least 70% of the opioid is released within 60 minutes in a USP Apparatus I, II or III in a relevant dissolution medium.

8. The formulation according to claim 1, wherein the active ingredient is susceptible to abuse.

9. The formulation according to claim 8, wherein the active ingredient is at least one active ingredient selected from opioids and morphine derivatives; antidepressants; stimulants; hallucinogenics; hypnotics; and tranquilizers, amphetamine, alprazolam, codeine, diazepam, fentanyl and analogs thereof, hydrocodone, hydromorphone HCI, lorazepam, meperidine, morphine, methylphenidate, methadone, nitrazepam, oxycodone HCL, oxymorphone, propoxyphene, temazepam, tramadol, zolpidem, and zopiclone.

10. The formulation according to claim 1, wherein the active ingredient is present in an amount ranging from about 0.05% w/w to about 30% w/w based on the total weight of the formulation.

11. The formulation of claim 1 having a viscosity of greater than 5000 cp.

12. A formulation according to claim 1, in a hard shell capsule, a gelatin capsule, or an hydroxypropyl methyl cellulose (HPMC) capsule.

13. The formulation according to claim 1, wherein the composition comprises from 60-80% w/w based on the total weight of the formulation of the carrier.

14. The formulation according to claim 1, wherein the composition comprises from 20-40% w/w based on the total weight of the formulation of a high acyl gellan gum.

15. The formulation according to claim 1, wherein the active ingredient is present in an amount ranging from about 0.05% w/w to about 20% w/w, based on the total weight of the formulation.

16. The formulation according to claim 1, wherein the active ingredient is present in an amount ranging from about 0.05% w/w to about 10% w/w based on the total weight of the formulation.

17. The formulation according to any of claim 1, 2-5 or 12-16, wherein the active ingredient consists of at least one active ingredient selected from opioids and morphine derivatives; antidepressants; hypnotics; and tranquilizers, alprazolam, codeine, diazepam, fentanyl and analogs thereof, hydrocodone, hydromorphone HCl, lorazepam, meperidine, morphine, methylphenidate, methadone, nitrazepam, oxycodone HCL, oxymorphone, propoxyphene, temazepam, tramadol, zolpidem, and zopiclone.

* * * * *